United States Patent [19]

Hofmeister

[11] Patent Number: 4,577,640

[45] Date of Patent: Mar. 25, 1986

[54] METHOD AND APPARATUS FOR DIRECT IN VIVO MONITORING OF UTERINE ELECTRICAL ACTIVITY

[76] Inventor: John F. Hofmeister, 3860 E. Easter Pl., Littleton, Colo. 80122

[21] Appl. No.: 591,530

[22] Filed: Mar. 20, 1984

[51] Int. Cl.$^4$ .............................................. A61B 5/05
[52] U.S. Cl. .................... 128/738; 128/642; 128/733; 128/734
[58] Field of Search .............. 128/639, 642, 709, 710, 128/731, 732, 733, 734, 738

[56] References Cited

U.S. PATENT DOCUMENTS

| | | | |
|---|---|---|---|
| 3,920,003 | 11/1975 | Ash et al. ........................ | 128/738 X |
| 3,924,609 | 12/1975 | Friedenberg et al. ............. | 128/738 |
| 4,050,079 | 9/1977 | Pegnim et al. ................... | 128/710 X |
| 4,396,019 | 8/1983 | Perry ................................ | 128/733 |
| 4,448,199 | 5/1984 | Schmid ............................. | 128/639 |

FOREIGN PATENT DOCUMENTS

584844 12/1977 U.S.S.R. .............................. 128/642

*Primary Examiner*—Edward M. Coven
*Attorney, Agent, or Firm*—Edwin L. Spangler, Jr.

[57] ABSTRACT

This invention relates to an improved apparatus for directly detecting and monitoring uterine bio-electrical activity "in vivo" characterized by an electrode carrier in the form of a cup shaped to conform to the patient's cervix and hold the electrodes contained therein in such intimate contact with the cervical tissue that an impedance match therebetween is established and maintained at a level of less than 10,000 ohms without the aid of suction. The invention is also characterized by non-invasive, broad-headed, low profile solderless electrodes. The invention is further characterized by the use of a multiple-electrode pattern containing at least three electrodes arranged such that separate and distinct current paths exist between each electrode and the others whereby discrete signals can be detected, monitored and charged. Additionally, the invention encompasses the novel method of measuring uterine electrical activity which comprises monitoring and recording the electrical potential along at least two discrete current paths simultaneously with reference to a common time base.

15 Claims, 13 Drawing Figures

METHOD AND APPARATUS FOR DIRECT IN VIVO MONITORING OF UTERINE ELECTRICAL ACTIVITY

Researchers have been studying the electrical activity of the uterus for 135 years. We now know that contractions of the uterine muscle in humans are initiated and regulated by electrical pulses which spread over the muscle fibers of the uterus. These electrical pulses are controlled by three reproductive hormones, namely estrogen, progestrone and possible luteinizing hormones. These hormones work together in a very precise phasic sequence during the menstrual cycle. The major hormone concentration shifts occur around mid-cycle at the time of ovulation.

Over the past 40 years there has been a major research effort to understand the effect of each of these hormones on the electrical activity of the uterus. There is now a very carefully done series of in vitro studies which have found multiple and often contradictory effects of these hormones on electrical activity in uterine muscle. By their very nature in vitro studies drastically alter many physiologic variables because they are performed on tissues isolated from the body and kept alive in saline solution, e.g. the blood supply is cut; nerve connections are severed; and hormone concentrations are washed out or diluted. What is needed to resolve these longstanding controversial findings is a method of in vivo recording which is sensitive enough to record electrical activity at mid-cycle. The apparatus used to measure the electrical activity of the uterus is known to physiologists, gynecologists and other skilled medical practitioners as an "electrohysterograph" (EHG).

The study of uterine bio-potential began in 1849 when DuBois Reymound found a weak electrical current in the uterine muscle of the rabbit. There followed a number of efforts to record and characterize the electrical patterns of the uterus in humans. In his review of these early studies Serr found very divergent results due primarily to widely differing methods and equipment, all of which is reported at pp. 65–80 in "Scientific Foundations of Obstetrics and Gynecology," editors: Philipp, E.E.; Newton, Michael, London. William Hevnemann, 1970. This early research was restricted by the technical difficulty of recording electrical activity in the microvolt range prior to the advent of modern electrical instrumentation.

In 1968 Serr et al reported on the use of a shielded needle electrode which was inserted at various sites and depths in the cervix, see Serr, D.M.; Porath-Fured et al, "Recording of Electrical Activity from the Human Cervix." J. Obstet, Gynec. Brit. Com., 75,360(1968). This method was abandoned because it was very painful for the subject and the needle wound itself resulted in a wound potential artifact. In this same investigation he found that a product known as a Perspex cervical cap with attached electrodes exhibited an unstable electrode-tissue resistance and a consequent unacceptable level of electrical interference. The best results were obtained with a vacuum cup electrode unit; however, the recordings did not show mid-cycle changes in electrical activity and most investigators consider this crucial to understanding the effect of female hormonal activity which demonstrates its maximum levels and fluctuations at mid-cycle. He did, however, find increased electrical activity during sexual stimulation and during pregnancy.

In 1968 Mannor et al (Mannor, S. M., Zakut, H., Serr, D. M., "Recording of Electrical Activity of the Human Uterus in the Presence of Intra-uterine Contraception Device." The VI International World Congress of Fertility and Sterility. June 1968) employed platinum-irridium electrodes mounted in an intrauterine device (IUD) to record electrical activity from the uterine cavity. They found three characteristic patterns of electrical activity. The drawback to this method was found to be the serious problem of differentiating normal uterine electrical activity from reactive electrical activity caused by the introduction of a foreign body into the uterine cavity.

Serr housed his electrodes in an ill-fitting standard size cervical cup and then applied suction thereto in an attempt to produce better contact between the cervical tissue and his electrodes. His efforts in this regard were only partially successful in that he ended up with a resistance of between 10,000 and 30,000 ohms which was apparently measured not by impedance but with a direct current resistance meter. While the lower end of this range is acceptable, a resistance of 8000 ohms or less is preferred.

The needle electrodes employed at one time by Serr et al penetrated the cervical tissues and proved to be painful to the subject to the extent that they became intolerable. The wound produced by invasion of the electrode produced artifact electrical spikes as well as a path by means of which bacteria could gain access to the tissues of the cervix and cause infection.

Serr also used non-invasive electrodes, however, little is reported about them in the literature. From what can be gleaned from the reports of Serr's work and that of his cohorts, his electrodes were rather long, cylindrical in shape with a diameter a great deal smaller than their height, and blunt-ended. Whatever their shape and size, the electrodes stuck up well above the surface of the cup and failed to make optimum electrical contact with the adjacent cervical tissue despite the fact that an attempt was made to suck these tissues up tight against the electrodes by applying a vacuum to the cup.

Serr and his co-workers contributed little in the way of useful information and uterine electrical activity since about all they learned was that it increased upon stimulation of the clitoris as well as during pregnancy. Such information has little clinical value and tells nothing about mid-cycle hormonal activity, anomalous patterns that would portend the presence of disease, impending miscarriage and other conditions that would be of value to a physician in both the areas of diagnosis and treatment. Serr et al did, however, clearly demonstrate that "in vivo" measurements of uterine electrical activity could be made at the site of the organ, i.e. directly as opposed to indirectly at some remote location on the body. Part of Serr et al's problems were probably a result of the unavailability of the sophisticated equipment we have available today; however, from what is known of their methodology, it very likely would have failed to reveal what my simultaneous multiple path methods show even with the best of modern equipment.

Measuring the electrical activity of other organs of the human body is, of course, commonplace in modern medicine. It obviously provides a useful diagnostic tool and oftentimes tells the physician not only what has happened but, in addition, what is likely to happen in the future that cannot be learned in any other way.

Late in the 19th century researchers developed a method of recording the electrical activity of the heart. Although the method was useful clinically, it was only with the pioneering work of Einthoven and others that the EKG became a major clinical tool. His concept was to record the EKG from several angles—The Einthoven Triangle. This enabled physicians to determine the vector angle of the cardiac electrical pulse and to see events which were not present on a single angle record. This method of recording is now standard procedure for the EKG.

Uterine electrical activity, however, is much more complex than the heart because there are multiple pathways, not just one. Normal cardiac electrical pulses follow a constant and predictable path through the heart. Initiating electrical pulses (pacemaker activity) are confined to one area in the heart. In the uterus, on the other hand, there are multiple sites of this activity. The spread of electrical pulses in the uterus is both diverse and exceedingly complex. Multiple electrodes near the heart show a simple wave form from several angles; whereas, I have discovered that several electrodes on the cervix spaced a few centimeters apart show very diverse and seemingly unrelated electrical activity. Accordingly, the preferred method for differentiating between these signals, therefore, requires simultaneous recording along two or more current paths.

Another factor differentiating my work from the conventional EKG is that my readings are taken directly from the organ in which the pulses are generated, not at a remote site on the outside of the body where such signals are attenuated, distorted and otherwise altered.

I have recently discovered that I can measure even mid-cycle uterine electrical activity by, first of all, precisely fitting the electrode-carrying cup to the subject's cervix, reshaping the tissue-contacting head of the electrodes into a low profile smooth-surfaced shallow dome-like button at least twice as wide as it is thick and, most significantly, using a minimum of three, and preferably four or more electrodes arranged in an unaligned pattern such that the current paths from one electrode to any of the others follow separate and distinct paths. By so doing, I am able to do away with the necessity for applying suction to the unit for the purpose of maintaining intimate stable contact between the electrodes and adjacent cervical tissue. Not only am I able to establish and maintain such contact, I do so without invading or otherwise traumatizing this most sensitive and delicate area of the body. The fit is so close, in fact, that I am consistently able to establish and maintain an impedance match of less than 10,000 ohms and usually between approximately 3000 and 8000 ohms.

While the equipment is important, and especially so since without it I could not record the minute voltages generated in the uterus, nevertheless, I feel my primary contribution may well be that of using at least three, and preferably four or more electrodes dispersed in an unaligned pattern such that readings can be taken along separate and distinct current paths. This is not the same thing as looking at the electrical activity of the heart from different angles because in the EKG, the same signal is seen from different perspectives. I have discovered that by taking these measurements along two or more different current paths, I can sometimes detect prominent electrical activity in one that is either not present or is at least of a magnitude I cannot as yet detect in the other. Even more significant, it seems to me, is that using two or more pairs of electrodes to take simultaneous readings unexpectedly reveals two entirely different signals, not one seen from different angles. In reality, the EKG is the sum of the electrical activity sensed as it reaches the remote electrodes after travelling there along several pathways. My methods, on the other hand, differ significantly in that I am apparently measuring discrete signals and thus have a method for differentiating as well as quantifying one from another. While precise location and orientation of these complex and diverse signals is not yet within my grasp, the method holds great promise even in this area. My pick-up is so sensitive and noise-free that I am able to clearly record the so-called "mid-cycle" electrical activity in the female reproductive system which, as matters now stand, at least appears to be vital information necessary to understand the effect of female hormones. My background investigation has failed to turn up a single researcher who was able to obtain these critical mid-cycle measurements using a cervical cup or cap equipped with electrodes as the electrical pick-up.

My pick-up also includes other features which, while incidental, are nonetheless important. To begin with, it has solderless crimped connections between the electrodes and the electrical leads thereto. Solder is highly toxic due to the presence of a certain amount of lead and, therefore, should the insulation covering a soldered connection break, the solder could dissolve in the acidic vaginal fluid. In addition, the offset potential between the dissimilar metals in the solder and the silver of the electrodes would be such as to swamp the offset rejection capability of the amplifier resulting in the recording system becoming ineffective.

In my system, I measure the electrode contact with the cervix using an impedance meter as opposed to a direct current resistance meter. I find that impedance measurement is more accurate for living tissue and, in addition, it avoids the problem of polarizing the electrodes which, if it happens, can have an adverse effect on their offset potential.

Finally, through a judicious selection and careful matching of available equipment, I am able to make the system completely safe for the subject. External skin contact electrodes require much less in the way of safety precautions than internal ones like those required for use inside the vagina. I accomplish this by providing two separate components, specifically, a current limiter and a so-called "optical isolation unit" built into the preamplifier that both provide electrical shock protection to the subject. The resulting integrated five-component system has enabled me to reliably record uterine electrical activity of as little as eight microvolts.

From a utilitarian standpoint, a strong correlation is already known to exist between uterine electrical activity and hormonal secretions, especially at certain times during the female menstrual cycle. My methods and apparatus already provide a physician like myself with tools and systems by means of which a pattern of electrical activity differing from the norm can be detected and thereafter used to correct the dysfunction causing same. In much the same manner as the EKG is used today, periodic uterine electrical activity plots on the same woman could be used to reassure her and her physician that she is functioning normally if the traces reveal no anomalies.

The effects of medication on the reproductive system and cause of sexual dysfunctions are definite possibilities. It may even be possible to monitor the cardiac bioelectrical activity of a fetus.

It is, therefore, the principal object of the present invention to provide a novel and improved pick-up apparatus for making stable essentially noise-free electrical contact with cervical tissues.

A second objective is that of providing a unique method of detecting and monitoring uterine electrical activity predicated upon charting such activity along two or more separate and distinct current paths, sometimes simultaneously and sometimes sequentially.

An additional object of the invention herein disclosed and claimed is to provide a multicomponent system for detecting and recording uterine bio-electrical activity that is so sensitive it is responsive to even mid-cycle potentials in the microvolt range.

Another objective of the within described invention is that of providing a close fitting cervical cup containing electrodes impedance-matched to the adjacent cervical tissue to within a range of approximately 3000 to 8000 ohms.

Still another object is to provide a unique low profile but broad-headed electrode of a non-invasive type ideally suited for use in a cup-shaped carrier for taking bio-electrical readings at the cervix.

Further objects are to provide a bio-electrical measurement and recording system of the class described which is simple, safe, accurate, reliable, easy to use, compact, electrically stable and easily adapted to a particular female subject.

Other objects will be in part apparent and in part pointed out specifically hereinafter in connection with the description of the drawings that follows, and in which:

Figure 1:
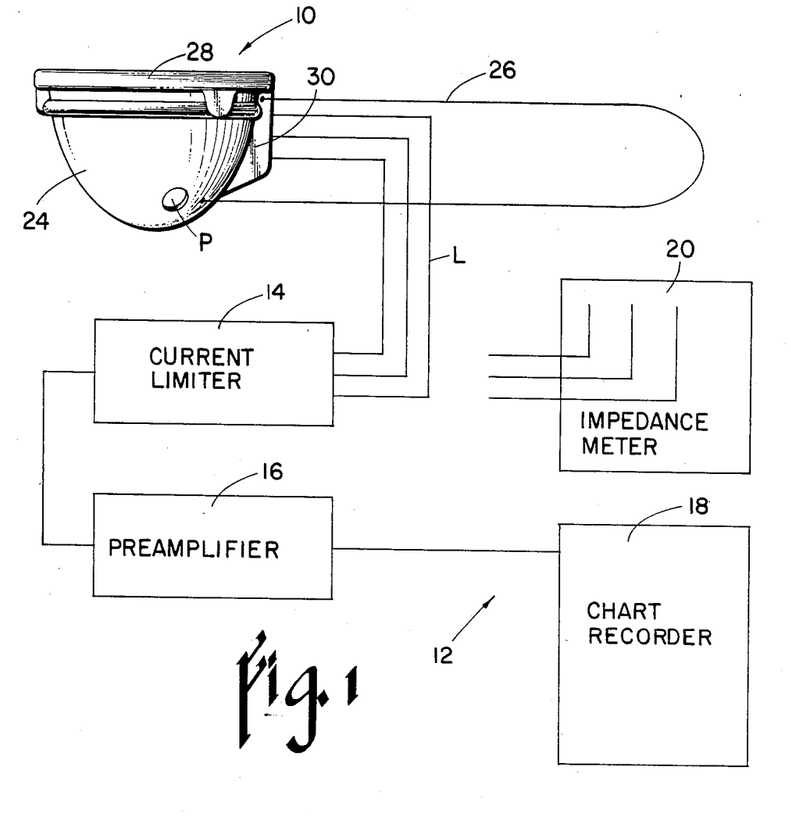
FIG. 1 is a schematic view showing the system used to both monitor and record the bio-electrical signals sensed by the pick-up when in intimate contact with the cervical tissue of a human female subject.

Referring next to the drawings and, initially, to FIG. 1 for this purpose, reference numeral 10 has been employed to broadly identify the pick-up device which senses to uterine bio-electrical activity at the cervix and transmits same by means of electrical leads outside the body through the vagina to a recording system generally indicated by numeral 12. Included in the recording system is a current limiter 14, a preamplifier 16 and a recorder 18. An impedance meter 20 is connected to the pick-up 10 just prior to making a recording and it is used to pass a minute AC current through the electrodes 22 and across the cervix for the purpose of measuring the electrical resistance (impedance) of the electrode/tissue interface. The impedance value displayed constitutes a verification of the physical and electrical contact of each electrode 22 with the adjacent cervical tissue. Impedances in the range of between approximately 3000 and 8000 ohms indicate satisfactory contact. Once contact has been thus verified, the impedance meter is disconnected and the pick-up reconnected to output into system 12. The impedance meter along with all the elements of the recording system 12 are all commercially available components.

The current limiter 14 is, in effect, a patient isolator that protects the subject from electrical shock by blocking any current greater than 50 microamperes. Uterine bio-potentials in the picoampere range pass through the patient isolator 14 unchanged to the preamplifier 16 which amplifies the signals 1000 times preparatory to delivering same to the recorder 18. The particular preamplifier I choose to use has a built in optical isolation unit which provides the subject with additional shock protection.

Recorder 18 is of the dual channel type which amplifies the signals and displays them on a strip of graph paper. One channel is sometimes used to record the EKG signal of the subject (not shown) which provides a constant input reference against which the uterine bio-electrical activity is plotted on the second of the two channels. As thus constituted, the system 12 together with my improved pick-up 10 when properly placed, will record uterine electrical activity of eight microvolts or greater.

The pick-up unit 10 which is unique and integral to the method is compatible with a wide range of clinical amplifiers and recording systems. It is relatively inexpensive, sterilizable, re-usable, and atraumatic to the tissues of the cervix even with repeated use on the same subject. The cervical cup 24 is available in graduated sizes and will fit almost any size and position of the cervix. The cervical cup slides onto the cervix easily, and can be inserted by either the clinician or the subject herself. This method does not cause any pain to the subject. Position of the cup on the cervix can be determined by manual palpation or under direct vision through a speculum. Electrode contact with the cervix can be verified and quantified by connecting an impedance meter 20 to the external wires of the cervical cup 24 as previously mentioned. Once in position the cup provides a very stable electrode/tissue impedance by means of a tissue cup interface. The unit can be easily removed after recording by first manually breaking the suction followed by gentle traction on nylon line 26 attached to the base of the cup.

Figures 2, 3:
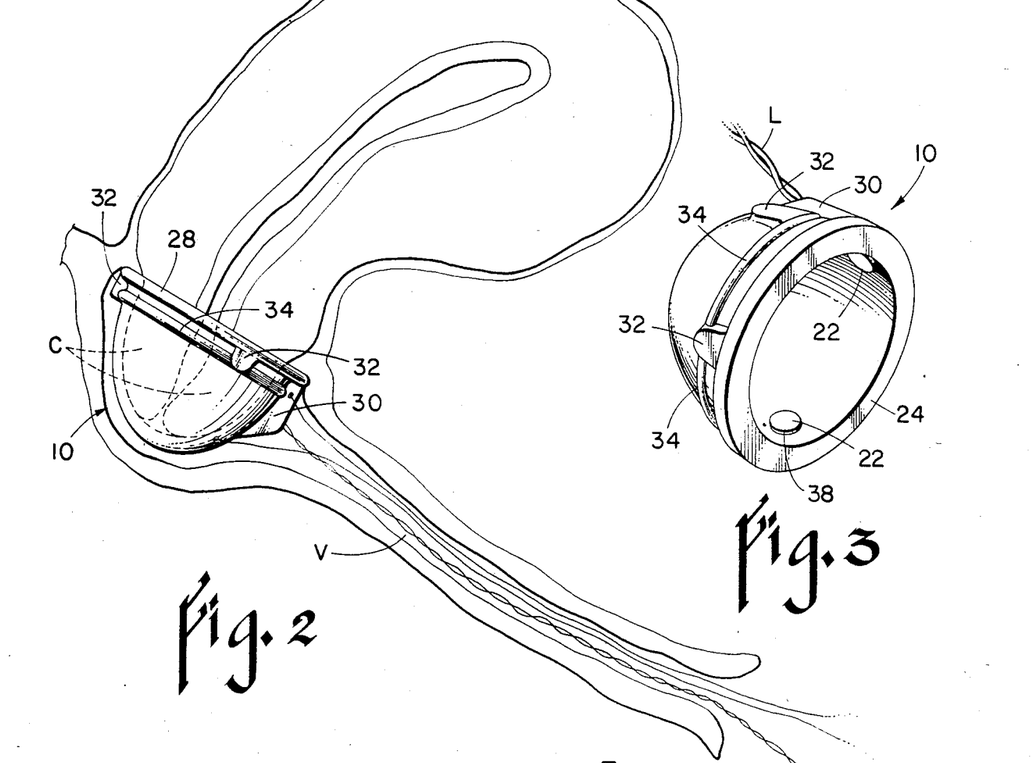
FIG. 2 is a view partially in elevation and partly in section showing the pick-up and associated parts thereof mounted in place upon the cervix.
FIG. 3 is a perspective view of the pick-up by itself to a slightly enlarged scale.

With specific reference to FIGS. 2–5, inclusive, it will be seen that cervical cup 24 is provided with a vent opening P, is marginally rimmed by integral flange 28 and, in addition, carries an external reinforcing boss 30 located beneath the latter that provides a convenient way of orienting the electrodes. The electrical leads L emerge from boss 30 also and it is oriented to face outwardly through the vagina V as shown in FIG. 2 when seated on the cervix C. The electrodes 22 are connected to the electrical leads L on the outside of the cup where they are covered by a silastic medical adhesive 32 which electrically insulates the connection from the adjacent vaginal wall and forms a dome-like cover over them. A similar silastic tunnel 34 houses the leads as they encircle the cup beneath the rim and enter the boss.

The cervical cup I use is a commercially available oligospermia cup designed to hold semen against the os of the cervix and thereby improve the chance of pregnancy. These cups are molded polyethylene available in several sizes. I find it most important to carefully match the size of this cup to the cervix of the subject since intimate contact of the electrodes 22 with the adjacent cervical tissues is essential for a good impedance match resulting in low-noise operation of the system.

Figure 6:
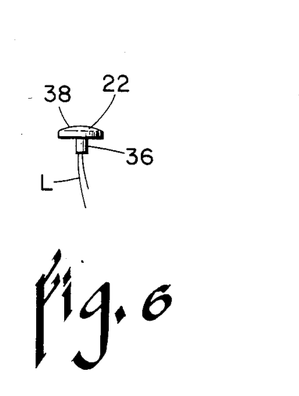
FIG. 6 is an elevational view showing one of the electrodes.

In FIG. 6 to which reference will next be made, electrode 22 can be seen to have a somewhat mushroom-shaped configuration consisting of a stem 36 topped by a head 38. Stem 36 is of a length to pass through the cup wall and emerge on the outside thereof where it is drilled to receive the leads L which are crimped in place. The head 38 of these electrodes is a good deal wider than it is thick. I have successfully used electrodes approximately 5 mm in diameter and 1.5 to 2 mm thick. These electrodes are machined from ingot grade silver and the exterior surface of the head exposed to the cervical tissues is polished and slightly rounded as shown to prevent mechanical trauma to the cervix. I use 38 gauge stranded, silver coated, Teflon-insulated wire for the leads L.

Figure 4:
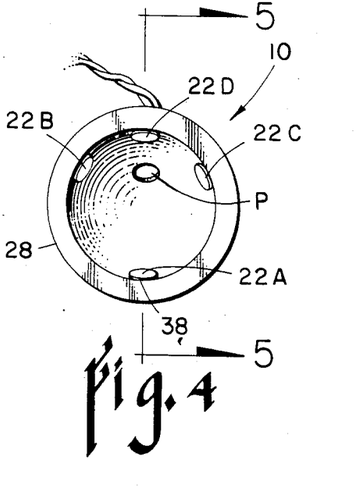
FIG. 4 is a front elevation of the pick-up.
Figure 5:
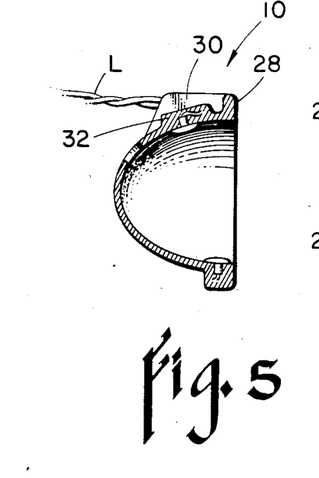
FIG. 5 is a diametrical section taken along line 5—5 of FIG. 4.

Looking next at FIGS. 3, 4 and 5, a pattern of electrode placement I have used successfully has been illustrated wherein three such electrodes identified as 22A, 22B and 22C are located at the corners of an equilateral triangle 120° apart and spaced the same distance beneath the rim. A fourth electrode 22D is located midway between two of the first three, specifically, 22B and 22C but offset beneath them as shown. By selecting different pairs I can detect and record the electrical activity along separate and distinct current paths, sometimes sequentially and at other times simultaneously.

Figure 7:
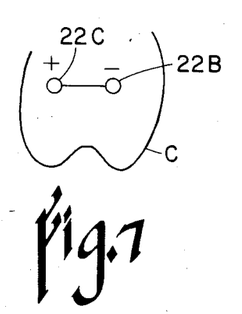
FIGS. 7–11, inclusive, are diagrams showing different electrode patterns and current paths established therebetween.
Figure 8:
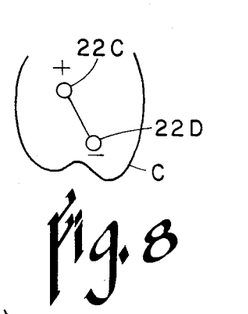
Figure 9:
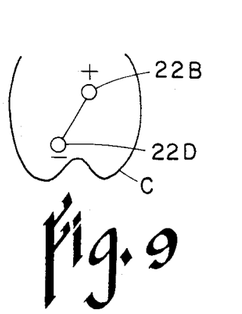
Figure 10:
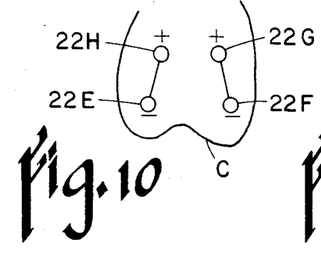
Figure 11:
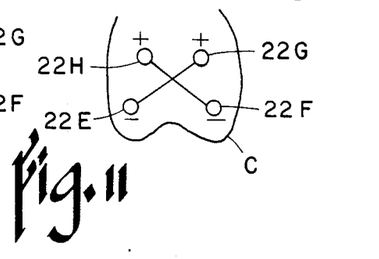

In the diagrams of FIGS. 7, 8 and 9, I show how electrodes 22B, 22C and 22D can be used to record the bio-electrical activity along three different current paths on one side of the cervix C of the subject. In FIGS. 10 and 11, on the other hand, I show a four electrode alternative pattern which I have successfully employed for simultaneous recordings. Here, electrodes 22E-22H are selectively connected as shown in FIG. 9 to provide simultaneous readings along side-by-side non-intersecting current paths and in FIG. 10 along crossed current paths.

The capabilities of my system to record the critical mid-cycle bio-electrical activity of the uterus and its close correlation with hormonal activity are clearly demonstrated by the following tables. In Table I, I have summarized in tabular form the results of my studies of hormone concentrations in one of several normal human females during her 26 day menstrual cycle. She had a negative gynecological examination and no history of any problems with her reproductive system. Recordings were taken every two or three days during the early follicular phase, daily during mid-cycle and then every few days until menses. Simultaneous blood samples were drawn for LH, extradiol and progesterone and the data appearing in Table I was normalized to the day of the LH peak (day 0).

TABLE I

| | HORMONE CONCENTRATION | | |
|---|---|---|---|
| Cycle Day | Estrogen pg/ml | Luteinizing Hormone MIU | Progesterone ng/ml |
| MENSTRUAL CYCLE | | | |
| 1 (−9) | — | — | — |
| 2 (−8) | — | — | — |
| 3 (−7) | 70 | 11 | too low to record |
| 4 (−6) | — | — | — |
| 5 (−5) | 108 | 11 | 0.01 |
| 6 (−4) | — | — | — |
| 7 (−3) | — | — | — |
| 8 (−2) | 269 | 9.7 | 0.01 |
| 9 (−1) | 337 | 39 | 0.4 |
| 10 (0) | 262 | 85 | 0.8 MID-CYCLE |
| 11 (+1) | 101 | 23 | 1.5 DAY |
| 12 (+2) | 68 | 17 | 4.2 Time of |
| 13 (+3) | 122 | 13 | 8.2 Ovulation |
| 14 (+4) | — | — | — |
| 15 (+5) | 164 | 7.8 | 15.2 |
| 16 (+6) | — | — | — |
| 17 (+7) | 226 | 9.1 | 16.5 |
| 18 (+8) | — | — | — |
| 19 (+9) | 205 | 5.7 | 14.4 |
| 20 (+10) | — | — | — |
| 21 (+11) | — | — | — |
| 22 (+12) | 155 | 7.6 | 12.0 |
| 23 (+13) | — | — | — |
| 24 (+14) | 90 | 6.9 | 5.1 |
| 25 (+15) | — | — | — |
| 26 (+16) | 30 | 8.4 | 0.7 |

The mid-cycle period is roughly from the sixth through the fourteenth day with the mid-cycle day being the tenth day of the cycle. Ovulation occurs approximately eighteen hours after the luteinizing hormone peak on the ninth day.

In Table II I have tabulated and averaged the wave frequency data taken from five subjects over five minute intervals.

TABLE II

| | WAVE FREQUENCY (5 minute periods) |
|---|---|
| Cycle Day | Total of Waves |
| 1 (−7) | 0 |
| 2 (−6) | 1 |
| 3 (−5) | 7 |
| 4 (−4) | 7 |
| 5 (−3) | 14 |
| 6 (−2) | 10 |
| 7 (−1) | 22 |
| 8 (0) | 4  MID-CYCLE DAY |
| 9 (+1) | 5  Time of Ovulation |
| 10 (+2) | 2 |
| 11 (+3) | 1 |
| 12 (+4) | 0 |
| 13 (+5) | 0 |
| 14 (+6) | 1 |
| 15 (+7) | 1 |
| 16 (+8) | 0 |
| 17 (+9) | 1 |
| 18 (+10) | 6 |
| 19 (+11) | — |
| 20 (+12) | 0 |

In Table II, it can be seen that the maximum electrical activities of these subjects occurred during mid-cycle which in this case covered the period between approximately the fourth through the twelfth day. The mid-cycle hormonal activity tabulated in Table I corresponds closely with the maximum mid-cycle electrical activity charted in Table II. More specifically, the recordings show irregularly spaced monophasic simple spikes of 0.2–0.5 sec. duration, and biphasic complex waves of variable duration. Wave amplitudes range from 2–800+ microvolts. The predominant pattern is a gradual increase in amplitude and frequency of both types of waves beginning about day −6 with a peak at day −1. On day 0 there is a sharp drop in frequency. Luteal phase activity is minimal except for a transient small increase in activity around day +10.

Figure 12:
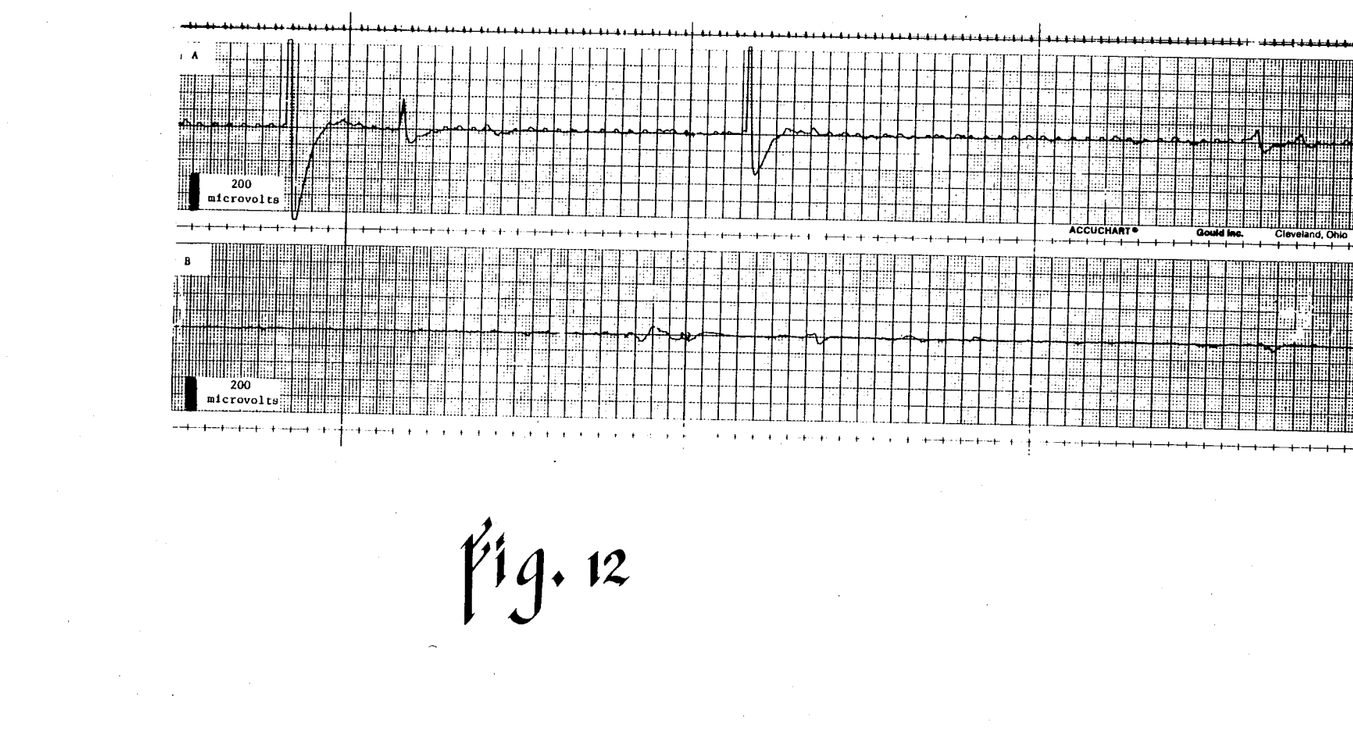
FIG. 12 is a simultaneous recording taken along the current paths of FIG. 10; and, FIG. 13 is a simultaneous recording similar to FIG. 12 except taken with the same electrode pattern as FIG. 10 but connected as shown in FIG. 11.
Figure 13:
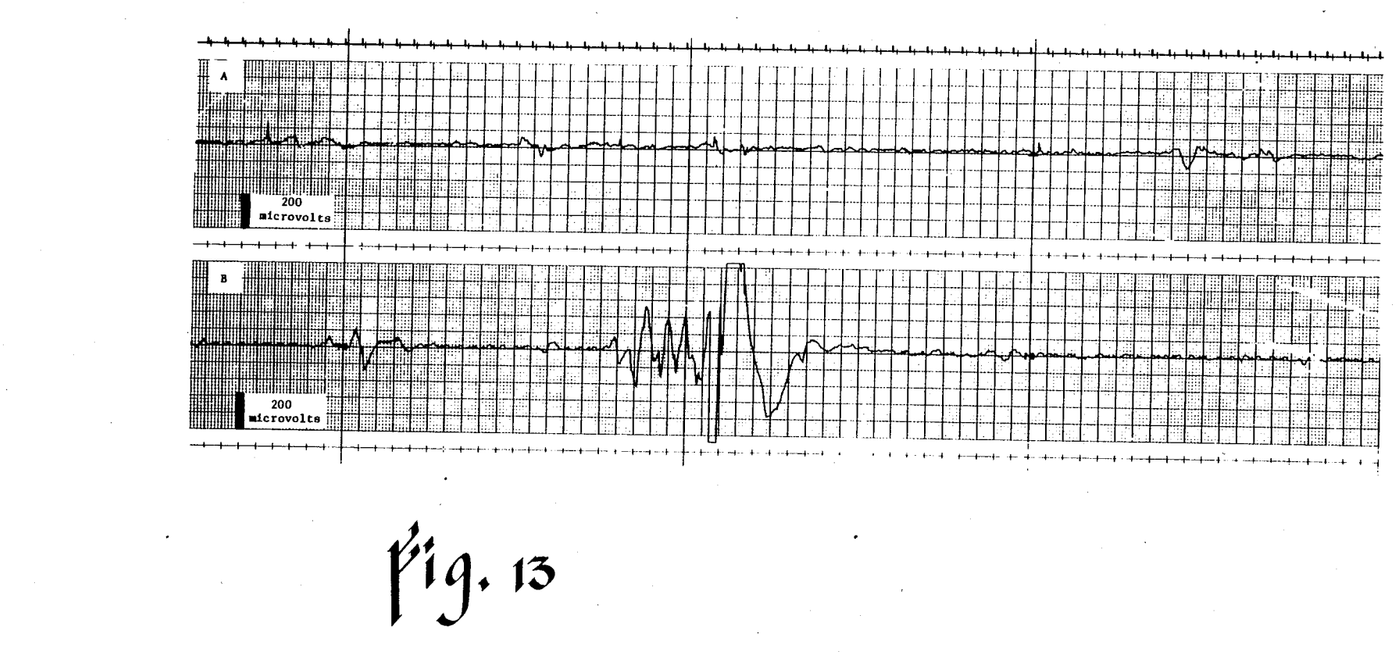

Prior to taking the recordings found in Table II above and in the charts of FIGS. 12 and 13, the pick-up unit 10 is washed in glassware detergent and then immersed in normal saline with the ends shorted together until the offset potential is less than 4 millivolts. This usually requires about five minutes. Then the unit is cold sterilized in Cidex for ten minutes, rinsed, and air dried.

The subject is placed in the lithotomy position on an examining table and the cervix is visualized with a single arm speculum. The cervix is wiped clear of secretions and then wiped with a cotton swab wetted with normal saline. The pick-up unit is then gently pushed into the vaginal canal until it slips on the cervix. Alternate methods of application include manual placement by either the clinician or the subject. Electrical contact of the electrodes 22 with the cervix is checked with the impedance meter 20. Electrode tissue impedance valves are characteristically less than 10K ohms, usually from 3K to 8K ohms. The pick-up unit is connected to the other components in a standard manner. Potential differences can be recorded across any two electrodes by varying the electrode leads attached to the actives of the current limiter 14.

Finally, referring to FIGS. 10 and 12, with a four electrode polygonal pattern connected as in FIG. 10, simultaneous readings were recorded on separate channels of the recorder as shown in FIG. 12, the trace at the top having been produced by the left-hand current path 22E–22H and the lower one by the right-hand current path 22F–22G. The bio-electrical activity seen along current path 22E–22H is, obviously, entirely different than that seen along the second current path 22F–22G. By using separate and distinct unaligned current paths I am able to isolate and record the bio-electrical activity in discrete areas of the cervix and the data supports the conclusion that I am not in any sense reading the same signal from two different vantage points as is the case with the EKG.

In FIGS. 11 and 13 I used the same electrode pattern as in FIG. 10 but reconnected them to provide crossing current paths 22E–22G and 22F–22H. Here again, the recording from electrodes 22F–22H at the top of FIG. 13 are entirely different from those of FIG. 12 as well as those at the bottom of FIG. 13 taken along current path 22E–22G.

Sequential recordings taken along these same current paths of FIGS. 10 and 11 would substantiate the fact that different signals are being sensed and recorded although, obviously, what is happening becomes much more apparent when simultaneous recordings are made. Sequential recordings made with a three-electrode triangular pattern of FIGS. 7, 8 and 19 reinforce and substantiate what is seen in the four-electrode two-path simultaneous recording of FIG. 13 although the individual signals differ, sometimes only in magnitude if the current paths closely follow one another to the extent that both are reading the same signal from slightly different positions. Changing the direction of the current path as it crosses or parallels the same signal has a definite effect upon its magnitude as seen on the chart. I am able, therefore, for the first time to isolate and record discrete bio-electrical signals by means of direct contact with the cervix using a pattern of at least three electrodes connected to define separate and distinct current paths. By increasing the pattern to include four electrodes, I can take simultaneous readings across selected pairs thereof and thus clearly differentiate one signal from another.

What is claimed is:

1. For use in a system for charting the uterine electrical activity in the human female, an improved pick-up which comprises: a cervical cup made of an insulating material shaped and sized to closely fit the cervix upon insertion into the vagina, at least three low profile metal electrodes having broad smooth-surfaced heads exposed inside the cup for contacting the adjacent cervical tissue with an impedance between each electrode and the tissue of the cervix of less than about ten thousand ohms, said electrodes being arranged in a non-linear pattern effective to provide at least two unaligned current paths defined by selected pairs of electrodes for detecting and monitoring any electrical activity between said selected pairs of electrodes and producing a signal corresponding to such electrical activity, means connected to each of said electrodes for separately conducting said signals outside the body, and means connected to said electrodes for recording each of said signals separately from other signals.

2. The pick-up as set forth in claim 1 wherein: the heads of the electrodes are generally dome-shaped.

3. The pick-up as set forth in claim 1 wherein: the heads of the electrodes are at least twice as wide as they are thick.

4. The pick-up as set forth in claim 1 wherein: three electrodes are used and arranged in a triangular pattern.

5. The pick-up as set forth in claim 1 wherein: four electrodes are used and arranged in a rectangular pattern.

6. The pick-up as set forth in claim 1 wherein: a lanyard accessible at the entrance to the vagina and connected to the cup provides means for removing the later.

7. The improved method for detecting and monitoring uterine bio-electrical activity in the body of a female which comprises: providing a cervical cup which is sized to closely fit the cervix upon insertion into the vagina, placing at least three electrodes formed of electrically conductive material on the cervical cup in a non-linear pattern effective to produce at least two unaligned current paths defined by selected pairs of electrodes, placing the cervical cup on the cervix with the electrodes contacting the cervix tissue and having an impedance between that tissue and the electrode of less than about ten thousand ohms, electrically connecting at least one pair of the electrodes together to define one current path, providing a first signal corresponding to electrical activity occurring in the one current path, conducting the first signal outside the body, selecting a second pair of electrodes different from the one pair, electrically connecting the second pair of electrodes together to define a second current path, providing a second signal corresponding to electrical activity occurring in the second current path, conducting the second signal outside the body, and recording each of said first and second signals separately from the other signal.

8. The improved method as set forth in claim 7 wherein: three electrodes are used, one electrode of the three is common to said one pair and said second pair thereof, and the electrical activity along said one and said second current paths is monitored sequentially.

9. The improved method as set forth in claim 8 wherein: the electrodes common to both said one pair and said second pair thereof is disconnected and the remaining two electrodes of the three electrically interconnected, and externally monitoring the electrical detected along a third current path between said remaining electrodes.

10. The improved method as set forth in claim 7 wherein: four electrodes are used and arranged in a rectangular pattern, and said one pair and said second pair of electrodes define non-intersecting current paths.

11. The improved method as set forth in claim 10 wherein: the electrical activity along said one current path and said second current path is monitored simultaneously.

12. The improved method as set forth in claim 11 wherein: the electricity along said one current path and said second current path is charted relative to a common time base.

13. The improved method as set forth in claim 7 wherein: four electrodes are used and arranged in a rectangular pattern, and said one pair and said second pair of electrodes define crossed current paths.

14. The improved method as set forth in claim 13 wherein: the electricity along said one current path and said second current path is charted relative to a common time base.

15. The improved method as set forth in claim 7 wherein: the impedance match between each electrode and the cervical tissue in contact therewith is between approximately 3000 ohms and approximately 8000 ohms.

* * * * *